(12) United States Patent
Hiles

(10) Patent No.: US 9,072,845 B2
(45) Date of Patent: Jul. 7, 2015

(54) CODED KEYING INSERT FOR MEDICAMENT CARTRIDGE

(75) Inventor: John Hiles, South Wirral (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 301 days.

(21) Appl. No.: 13/642,080

(22) PCT Filed: Apr. 21, 2011

(86) PCT No.: PCT/EP2011/056480
§ 371 (c)(1),
(2), (4) Date: Feb. 25, 2013

(87) PCT Pub. No.: WO2011/131781
PCT Pub. Date: Oct. 27, 2011

(65) Prior Publication Data
US 2013/0150786 A1  Jun. 13, 2013

Related U.S. Application Data

(60) Provisional application No. 61/327,296, filed on Apr. 23, 2010.

(30) Foreign Application Priority Data

Jul. 29, 2010 (EP) .................................... 10171168

(51) Int. Cl.
*A61M 5/00* (2006.01)
*A61M 5/50* (2006.01)
(Continued)

(52) U.S. Cl.
CPC ............... *A61M 5/5086* (2013.01); *A61J 1/062* (2013.01); *A61J 2205/40* (2013.01); *A61M 5/24* (2013.01); *A61M 5/3134* (2013.01);
(Continued)

(58) Field of Classification Search
CPC .......... A61M 2205/6045; A61M 5/24; A61M 5/3134; A61M 5/5086
USPC ........................................................ 604/111
See application file for complete search history.

(56) References Cited

U.S. PATENT DOCUMENTS 5,069,225 A * 12/1991 Okamura ....................... 600/578
5,334,162 A *  8/1994 Harris .......................... 604/232
(Continued)

FOREIGN PATENT DOCUMENTS

DE      20110690      9/2001
WO      93/20869      10/1993
(Continued)

OTHER PUBLICATIONS

International Search Report for Int. App. No. PCT/EP2011/056480, completed May 27, 2011.
(Continued)

*Primary Examiner* — Aarti B Berdichevsky
(74) *Attorney, Agent, or Firm* — McDonnell Boehnen Hulbert & Berghoff LLP

(57) ABSTRACT

A keying insert for use with a cartridge assembly containing a fluid. The insert comprises a main body defining a bore that extends from a proximal end to a distal end of the main body and allows the fluid to dispense from the distal end of the cartridge through a septum. The main body includes a septum for sealing the fluid within the cartridge and a coding feature that is keyed to a cartridge holder or other dispense interface.

19 Claims, 2 Drawing Sheets

(51) Int. Cl.
  *A61M 5/24*   (2006.01)
  *A61J 1/06*   (2006.01)
  *A61M 5/31*   (2006.01)
  *A61M 5/315*   (2006.01)
(52) U.S. Cl.
  CPC ......... *A61M 5/31551* (2013.01); *A61M 5/3158* (2013.01); *A61M 2005/2407* (2013.01); *A61M 2205/6045* (2013.01); *A61M 2205/6081* (2013.01)

(56) References Cited

U.S. PATENT DOCUMENTS 5,435,076 A * 7/1995 Hjertman et al. ............... 34/296
2003/0109835 A1 * 6/2003 Woolston et al. ............. 604/232
2010/0152669 A1 * 6/2010 Rosenquist ................... 604/192

FOREIGN PATENT DOCUMENTS

WO          02/11664       2/2002
WO        2008/033141      3/2008

OTHER PUBLICATIONS

International Preliminary Report on Patentability for Int. App. No. PCT/EP2011/056480, mailed Apr. 23, 2010.

* cited by examiner

CODED KEYING INSERT FOR MEDICAMENT CARTRIDGE

CROSS REFERENCE TO RELATED APPLICATIONS

The present application is a U.S. National Phase Application pursuant to 35 U.S.C. §371 of International Application No. PCT/EP2011/056480 filed Apr. 21, 2011, which claims priority to U.S. Provisional Patent Application No. 61/327,296 filed Apr. 23, 2010 and European Patent Application No. 10171168.7 filed Jul. 29, 2010. The entire disclosure contents of these applications are herewith incorporated by reference into the present application.

FIELD OF INVENTION

The present disclosure is generally directed to reservoirs, particularly reservoirs containing a medicament. More particularly, the present disclosure is generally directed to a coded keying insert for use with a reservoir and a reservoir holder so as to prevent unwanted reservoir cross use. As just one example, such medicament reservoirs may comprise an ampoule, a cartridge, a vial, or a pouch, and may be used with a medical delivery device. Exemplary medical delivery devices include, but are not limited to syringes, pen type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder is disconnected from the drug delivery device and the empty cartridge is removed and replaced with a new cartridge. Most suppliers of such cartridges recommend that the user dispose of the empty cartridges properly. Where the drug delivery device comprises a disposable device, once the cartridge is empty, the user is recommended to dispose of the entire device.

Such known self-administration systems requiring the removal and reloading of empty cartridges have certain limitations. For example, in certain generally known systems, a user simply loads a new cartridge into the delivery system without the drug delivery device or without the cartridge having any mechanism of preventing cross use of an incorrect cartridge. That is, the drug delivery device does not have a mechanism for determining if the medicament contained in the cartridge is indeed the correct type of medicament to be administered by the patient. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and manufactured to comply with certain recognized local and international standards. Consequently, such cartridges are typically supplied in standard sized cartridges (e.g., 3 ml cartridges). Therefore, there may be a variety of cartridges supplied by a number of different suppliers and containing a different medicament but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, caregivers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device. Likewise, there is a general need to physically dedicate or mechanically code a cartridge to its drug type and design an injection device that only accepts or works with the dedication or coded features provided on or with the cartridge so as to prevent unwanted cartridge cross use. Similarly, there is also a general need for a dedicated cartridge that allows the medical delivery device to be used with only an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e., making it more difficult for counterfeiters to provide unregulated counterfeit medicament carrying products.

It is an aim to provide means for a cartridge that reduces the potential risk of a user loading an incorrect drug type cartridge.

SUMMARY

This aim is achieved by a keying insert for use with a cartridge, the keying insert defining a bore, which is configured for receiving a septum. The keying insert is configured to form a seal within a cartridge containing a fluid. The keying insert comprises a pass through to allow dispensing of the fluid from the cartridge and a coding feature being configured to cooperate with a corresponding coding feature provided by a fluid delivery device.

In one embodiment, the keying insert comprises a main body defining the bore, the main body extending from a proximal end to a distal end and where the bore is configured for receiving a septum. A side wall extends from the proximal end to the distal end and at least a portion of the side wall is configured to form the seal within the cartridge. The coding feature is located on the main body.

In another embodiment, the keying insert comprises a main body defining the bore, the main body extending from a proximal end to a distal end. The bore is configured for receiving a septum; a side wall extending from the proximal end to the distal end. At least a portion of the side wall is configured to form the seal within the cartridge. A second body is in sealing relationship to the main body, wherein the coding feature is located on the second body.

The keying insert is for use with a cartridge assembly containing a fluid. The keying insert is suitable for sealing the distal opening of a cartridge so that fluid cannot pass between the side wall of the keying insert and the inner wall of the cartridge. The bore allows the fluid to dispense from the distal end of the cartridge through a septum which may be located in the bore.

A distal end of a device or a component thereof is closest the dispensing end of the device. A proximal end is the end of the device or a component thereof which is furthest away from the dispensing end of the device. The keying insert can be comprised of a single main body or a combination of bodies. If the keying insert comprises only a single main body, other body elements are not provided. If the keying insert comprises a combination of bodies, at least a main body and a second body are provided. A fluid delivery device, preferably a drug delivery device, may be a device designed to dispense a selected dose of a fluid, preferably a drug, e.g. insulin, insulin analogues, growth hormones, heparins and their derivates etc., optionally suitable for self-administration. The dose may be fixed or variable. The device may be of mechanical type or may comprise electronic elements. The device may be a mobile, hand-held device, e.g. a drug delivery pen type device. The device may be disposable or reusable. The device may be a fluid dispense interface wherein the interface is suitable for dispensing a selected dose. The device and the interface are suitable for holding a cartridge assembly containing a drug that can be administered via a needle. The device or the interface comprises optionally a cartridge holder, which may be an element of the device or the interface. Alternatively the cartridge assembly may be held by an integral part of a housing of the device or the interface. A cartridge assembly has tube made e.g. of glass and forming the cartridge and a moveable bung that is provided at the proximal end. The keying insert seals a distal opening of the cartridge. The coding feature on the keying element engages with the coding feature on the device or the interface. In one embodiment, one of the coding features is formed as protrusion and the other one as a cavity, e.g. slots engaging corresponding ribs or splines.

According to an exemplary arrangement, a keying insert for use with a cartridge comprises a main body that defines a bore, where the main body extends from a proximal end to a distal end and where the bore is configured for receiving a septum. A side wall extends from the proximal end to the distal end, where at least a portion of the side wall is configured to form a seal within the distal end of the cartridge containing a fluid. There is a pass through in the distal end of the main body that allows dispensing of the fluid from the cartridge. There is also a coding feature located on the distal end of the main body that is configured to cooperate with a corresponding coding feature on a fluid delivery device or on fluid dispense interface or on both.

In another arrangement, a keying insert for use with a cartridge comprises a main body defining a bore, where the main body extends from a proximal end to a distal end and where the bore is configured for receiving a septum. The main body also has a side wall that extends from the proximal end to the distal end and where at least a portion of the side wall is configured to form a seal within a cartridge containing a fluid. There is a pass through in the distal end of the main body to allow dispensing of the fluid from the cartridge. There is also a second body in sealing relationship to the main body and a coding feature located on second body that is configured to cooperate with a corresponding coding feature provided by a fluid delivery device or fluid dispense interface or both. Sealing relationship means that the fluid cannot pass between the main body and the second body, which may be connected to each other by any suitable means. In one embodiment the main body and the second body are merely pressed to each other, thereby forming a sealing relationship.

The keying insert and a cartridge assembly may be used with a drug delivery device. The cartridge assembly comprises a tubular barrel, said tubular barrel comprising a bung located near a proximal end of said tubular barrel and a neck portion defining a distal port and having an interior wall, where the keying insert cooperates with the interior wall of the tubular barrel to form a seal, where the coding feature is located on a distal end of the keying insert protruding from the neck portion.

In one embodiment, a fluid delivery system comprises a keying insert, a cartridge assembly and a drug delivery device.

In yet another embodiment of there is a cartridge assembly for use with a drug delivery device comprising a tubular barrel having a bung located near a proximal end of the tubular barrel and a neck portion defining a distal port and having an interior wall. There is a keying insert configured to cooperate with the interior wall to form a seal, where the keying insert may have a coding feature located on a distal end protruding from a neck portion. That keying insert has a coding feature that may be configured to cooperate with a corresponding coding feature on a cartridge holder of a fluid dispensing device.

The keying insert may include a pierceable septum. The septum seals the bore. During the drug delivery the septum may be pierced by a needle, so that the drug may be delivered through the needle. In one embodiment the septum seals the bore again after removing the needle. The septum allows a dispense interface, such as a double ended needle cannula, to be in fluid communication with the contents of the cartridge when the dispense interface is attached to a device holding the cartridge. Main body and septum may be molded from the same materials. The keying insert can also have one or more indicia to identify the fluid contained with the cartridge or to identify a corresponding fluid delivery device. These indicia, which serve as markings, can include color, tactile, smell, text, numbers, symbols, and any number of combinations of these and is located on the distal the distal end of the keying insert that extends outside of the cartridge, which enable different types of sensory perception. In one embodiment the indicia are located on a distal end of the main body extending outside of the cartridge. In another embodiment the second body comprises indicia to identify the fluid contained with the cartridge or to identify a corresponding fluid delivery device. The indicia may be located on a portion of the second body that extends outside of the cartridge.

The keying element maybe comprised of multiple bodies, each having various materials of construction. In one embodiment the keying insert has a main body and a second body in sealing contact with each other where the second body comprises a material of construction that is harder/stiffer than the main body material of construction. In such a design the material of construction of the main body is selected from, but not limited to, the group comprising natural rubber, synthetic rubber, polyurethane, and mixtures thereof. Further, the material of construction of the second body is selected from, but not limited to, the group comprising rubber, polyurethane, polyacetal (Delrin), acrylonitrile butadiene Styrene (ABS), polypropylene and mixtures thereof. A preferred combination is where the main body comprises rubber and the second body comprises polyacetal.

The coding feature and/or indicia may be located on one or more of the bodies that make up the keying insert. A portion of the proximal end of the keying insert may be within the cartridge and a portion of the distal end may be outside of the cartridge. The indicia may be located on the distal end of the main body that extends outside of the cartridge. The coding feature may be provided along an end face of the second body. A portion of the second body may be outside of the cartridge. Regardless of number of bodies making up the keying insert there will be a portion of the proximal end that is always within the cartridge, preferably at the distal end or neck portion of the cartridge. Likewise, there will be a portion of the distal end of the keying insert that is always protruding outside of the cartridge.

The coding feature can be provided along an end face and/or side wall of the keying insert and can include a plurality of indentations, slots, grooves, protrusions, splines or any combination of these or like physical features that cooperate with corresponding coding features located on a cartridge holder, fluid dispensing device, dispense interface or a combination of these. The keying insert can also have a releasable coupling for mounting a dispense interface, such as a needle assembly. The releasable coupling may contain a thread for attaching a needle assembly. Preferably, the coding feature of the keying insert prevents the cartridge from rotating within a cartridge holder of a fluid deliver device.

The terms "medicament" or "drug", as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

These as well as other advantages of various aspects will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1:
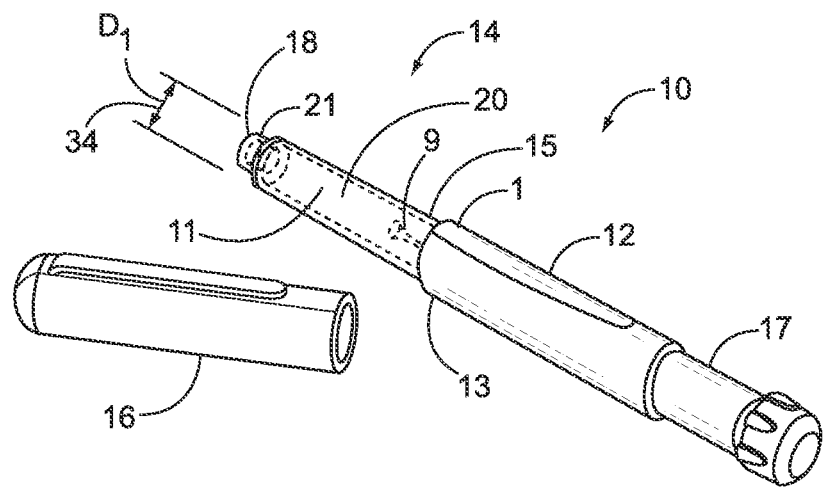
FIG. 1 illustrates an exemplary pen type drug delivery device.

Referring to FIG. 1, there is shown one of many possible types of a drug delivery device 10 in the form of a pen type syringe. This drug delivery device 10 comprises a dose setting mechanism 12, a cartridge holder 14, and a removable cap 16. A proximal end 15 of the cartridge holder 14 and a distal end 13 of the dose setting mechanism 12 are removably secured together. The pen type syringe may comprise a re-usable or a disposable pen type syringe. Where the syringe comprises a re-usable device, the cartridge holder 14 and the dose setting mechanism are removably coupled together. In a disposable device, they are permanently coupled together. In FIG. 1, the dose setting mechanism 12 comprises a piston rod 9, such as a threaded piston rod that rotates when a dose is injected.

To inject a previously set dose, a double ended needle assembly (not shown) is attached to a distal end 18 of the cartridge holder. Preferably, the distal end 18 of the holder comprises a thread 21 (or other suitable connecting mechanism such as a snap lock, snap fit, form fit, or bayonet lock mechanism) so that the needle assembly may be removably attached to the distal end 18 of the cartridge holder. When the drug delivery device 10 is not in use, the removable cap 16 can be releasably retained over the cartridge holder 14.

Figure 2:
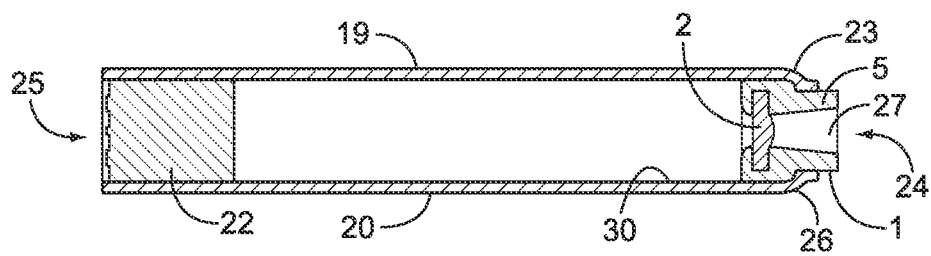
FIG. 2 illustrates a sectional side view of a cartridge that includes the keying insert that may be loaded into a cartridge holder of the pen type drug delivery device illustrated in FIG. 1.

An inner cartridge cavity 11 defined by the cartridge holder 14 is dimensioned and configured to securely receive and retain the cartridge assembly 20 comprising a glass cartridge 19 having bung 22 (see FIG. 2). Typically, the cartridge 19 is manufactured of glass and includes a generally tubular barrel extending from a distal end 24 to a proximal end 25 and having a neck portion 23, which is of a smaller diameter neck than the tubular barrel. This neck projects distally from the shoulder 26 of the barrel. Inside the neck is the keying insert 1. The proximal portion of the keying insert 1 is in a sealing relationship with the inner wall 30 of the tubular barrel and the distal portion of the keying insert 1 projects outwardly from the distal end/opening of cartridge assembly 20.

Figure 4:
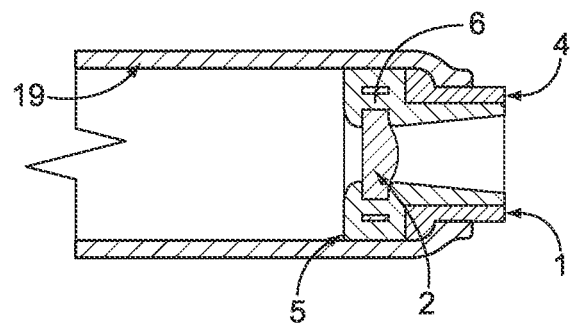
FIG. 4 illustrates a sectional side view of the distal end of a cartridge showing one embodiment of the keying insert having two bodies and a septum.
Figure 5:
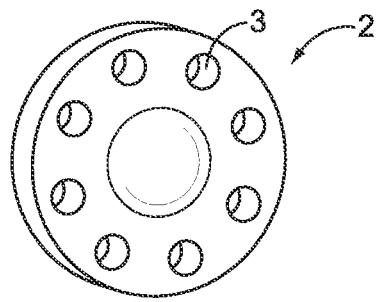
FIG. 5 illustrates one embodiment of a septum design for over-molding with a main body.
Figure 6:
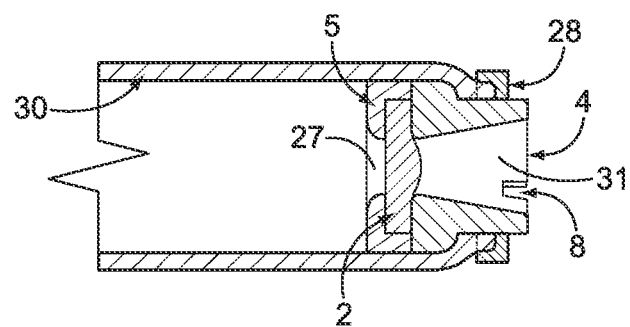
FIG. 6 illustrates a sectional side view of the distal end of a cartridge showing one embodiment of the keying insert having two bodies and a septum.

The keying insert 1 can be comprised of a single main body 5 or a combination of bodies, such as a main body 5 and second body 4 (see FIG. 4). Preferably main body 5 is configured to have an opening or bore 27 and to accept a pierceable seal or septum 2 that seals bore 27. Septum 2 is securely held across bore opening 27 by any means that provides a seal between the contents of the cartridge and outside environment. Main body 5 and septum 2 can be molded from the same materials, preferably rubber. A preferred means to secure the septum 2 to the main body 5 includes over-molding of the main body 5 to the septum 2 as illustrated in FIGS. 2 and 4. This can be achieved by using a septum 2 as depicted in FIG. 5 that has holes/openings 3 around the circumference of the septum 2 to allow a portion of the main body 6 to flow through during the over-molding process, sometimes referred to as "pinning." Alternatively, the septum 2 can be held in place by a press fit or "sandwiched" between the main body 5 and a second body as illustrated in FIG. 6.

Figure 3:
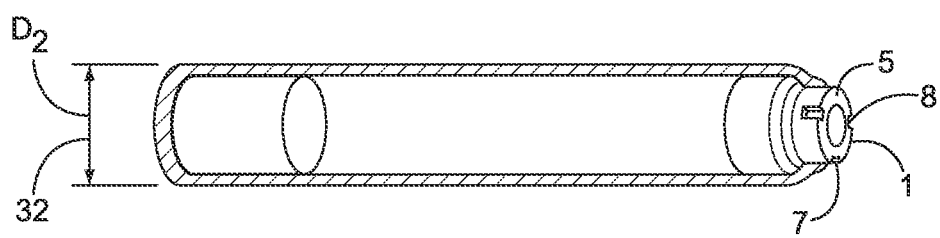
FIG. 3 illustrates a perspective view of a glass cartridge illustrated in FIG. 2 with the keying insert having a color indicia on the coding feature.

The keying insert 1 contains coding features that cooperate with corresponding coding features on a fluid delivery device or dispense interface. Preferably, such a device with have a cartridge holder 14 that accepts the coding feature of the keying insert 1. Any type of coding feature will work with the keying insert 1, such as the slots 8 shown in FIGS. 3 and 6. These slots 8 would engage corresponding ribs or splines or other protrusions located at the distal end inside a cartridge holder 14. FIG. 3 also illustrates the use of indicia on the keying insert 1, in this case color 7 placed in each of the slots 8. Such indicia allow the user to readily identify the type of medicament contained in the cartridge 19 and/or to match the cartridge 19 to a specific injection device.

In some cases it might be necessary for the coding feature to be made of a harder material than the main body 5. FIGS. 4 and 6 illustrate two possible embodiments where a second body 4 is constructed of a harder material than main body 5 to provide for greater support and integrity of the coding feature. The softer more compliant main body 5 can be used to "sandwich" the harder second body 4 into a press sealing fit with the inner wall 30 of the cartridge. FIG. 6 also illustrates an embodiment where a retaining ring 28 can be used to further secure the keying insert 1 into the cartridge 19. Retaining ring 28 can be made of any known materials that will form a tight fit to the outer wall of the neck portion 23 of the cartridge. Acceptable materials include metals that can be crimped around a circumferential bead at the distal end of the neck. In addition, it is possible to include coding features on the retaining ring 28 that are in addition to, or an extension of, the coding features on the keying insert 1.

Placement of the keying insert 1 into a cartridge 19 can be accomplished in a number of ways known to those skilled in the art of manufacturing such cartridge assemblies 20. One particularly preferred way is to first insert the keying insert 1 into the proximal end of the empty cartridge 19 by pushing it part way towards the distal end. Next, the desired amount of fluid is added to the cartridge 19 and a stopper or bung 22 is then fitted into the proximal end of the cartridge barrel. Bung 22 is in sliding fluid-tight engagement with the inner tubular wall of the barrel. This bung 22 is then pushed axially in the distal direction by a mechanical device, which pressurizes the fluid that in turn forces the keying insert 1 to move forward to the neck portion 23 of the cartridge where it will seat in a sealing form-fit engagement with the inner wall 30 of the cartridge. The bung 22 is preferably designed to prevent air from being trapped with the fluid during this process. Once filled a paper, film or foil could be added to end of the keying insert 1 to maintain sterility until inserted in a fluid dispensing device 10. Because the proximal end of the keying insert 1 that is within the cartridge 19 can be configured to exactly form-fit to the inner shape of the neck portion 23 of the cartridge the amount dead space obtained is greatly minimized in the neck portion 23 compared to traditional cartridge assemblies. This saves the costs associated with wasted, unusable medicament trapped in the dead space.

Axially directed forces acting upon the stopper 22 during dose injection or dose administration urges the fluid from the cartridge 19 though a dispensing interface, such as a double ended needle, mounted onto the distal end 18 of the cartridge holder 14. Such axially forces may be provided by piston rod 9 working in unison with dose setting member 12. Alternatively, the dispensing interface may be connected and in some cases coded directly to the keying insert 1. For example, bore 27 or annulus 31 within the second body 4 could contain threads or other type of connector to allow a dispensing interface to be securely and sealably attached.

A portion of the cartridge holder 14 defining the cartridge holder cavity 11 is of substantially uniform diameter represented in FIG. 1 by D1 34. This diameter D1 34 is preferably slightly greater than the diameter of the cartridge assembly 20. The interior of the cartridge holder 14 can include an inwardly-extending annular portion or stop that is dimensioned to prevent the cartridge assembly 20 from moving within the cartridge holder 14. In this manner, when the cartridge assembly 20 is loaded into the cavity 11 of the cartridge holder 14 and the cartridge holder 14 is then connected to the dose setting member 12, the cartridge assembly 20 will be securely held within the cartridge cavity 11.

A number of doses of a medicament may be dispensed from the cartridge assembly 20. Preferably, the cartridge assembly 20 contains a type of medicament that must be administered often, such as one or more times a day. One such medicament is insulin.

The dose setting mechanism 12 comprises a dose setter 17 at the proximal end of the dose setting mechanism. In one preferred arrangement, the dose setter 17 is rotated to set a dose. To administer this set dose, the user may attach a needle assembly comprising a double ended needle on the distal end of the cartridge holder 14. In this manner, the needle assembly pierces the seal 2 of the keying insert 1 and is therefore in liquid communication with the medicament. The user pushes on the dose setter 17 to inject the set dose. The same dose setting and dose administration procedure is followed until the medicament in the cartridge assembly 20 is expended and then a new cartridge assembly 20 must be loaded in the device. To exchange an empty cartridge assembly 20, the user is called upon to remove the cartridge holder 14 from the dose setting mechanism 12.

Employing a molded keying insert 1 offers a number of advantages. For example, a molded keying insert may enable a more robust and finer coding scheme than could be applied to a metal keying insert. For example, the keying insert 1 may comprise a plastic such as PP, acetal, polyamide, polyacetal (Delrin), ABS, or, alternatively, a metal such as zinc, magnesium or aluminium. In addition, a molded keying insert 1 may be used with standard glass cartridges, such as the glass cartridge 19 illustrated in FIGS. 2 and 3. Because this standard cartridge need not be modified, the keying insert 1 can also reduce cost and technical risk because modification to the glass ampoule, development and investment in new cartridge manufacturing production equipment, and development of new manufacturing processes is unnecessary.

The keying insert 1 comprises a basically cylindrically shaped main body 5 defining a centrally located bore 27. The outer diameter of the proximal portion of the main body 1 is generally greater that the diameter of the distal portion. This allows the keying insert 1 to extend outwardly from the distal end of the cartridge 19. An alternate embodiment is shown in FIG. 6 where the main body 5 is used to secure a second body 4 within the neck of the cartridge 19. In this embodiment the proximal portion of the second body 4 has a greater diameter than the distal portion that protrudes outwardly from the cartridge 19. The bore 27 or annulus 31 provides a needle assembly access to at least a portion of seal 2.

Preferably, the distal keying insert 1 comprises coding features and these coding features could be applied in various positions and/or locations on the keying insert 1. For example, the outer or side walls of either the main body 5 or the second body 4 are used to locate the desired coding features. Likewise, the distal end faces of the bodies 4, 5 can contain the coding features. As just one example, as best seen in FIG. 3, the coding feature is in the form of a plurality of slots 8 provided along the side wall of the main body 5 or along the side wall of the second body 4 as shown in FIG. 6. Although only three slots 8 are illustrated in this preferred arrangement, those of skill in the art will recognize alternative arrangements may also be provided, and they may or may not be equally sized or equally spaced around the circumference. These slots 8 are arranged so that they will cooperate with a cartridge holder 14 that includes a cooperating coding mechanism, such as ribs or splines that engage or form a coupling with the slots. In this manner, when the cartridge assembly 20 carrying the keying insert 1 is inserted into the cartridge holder 14, the slots 8 of the keying insert cooperate with the distal end projections in the cartridge holder 14 such that the keying insert 1 and therefore the cartridge assembly 20 can reside in a final seated position.

One advantage of utilizing a plurality of slots 8 or other indentations along an end face or side wall of the keying insert 1 in combination with the raised features in the cartridge holder 14 is that such a coding scheme prevents a standard cartridge assembly from being used with the coded cartridge holder 14. For example, if a user tried to insert a non-coded cartridge assembly into the coded cartridge holder 14, the protrusions would prevent the cartridge assembly from residing in a final seated position. Consequently, since the keying insert 1 would not fully abut the corresponding coding feature of the cartridge holder 14 the cartridge 19 would protrude too far out of the holder, thereby preventing assembly of the cartridge holder 14 to the dose setting member of the device 10.

Another advantage of the keying insert 1 is that it prevents rotation of the cartridge assembly 20 when a double ended needle is mounted onto the distal end of the cartridge holder 14 which may occur by threading the needle assembly onto a receiving thread at the distal end of the cartridge holder 14. In addition, it also prevents rotation of coding features relative to cartridge 19. While inserting the cartridge assembly 20 into the holder 14, the user is required to hold the cartridge assembly 20 in order to align the coding features. Therefore, if the coding features were allowed to rotate relative to cartridge 19, it would be difficult to align these coding features.

Although aimed primarily at the insulin market, the keying insert 1 may apply to other drugs. It may apply to various devices, including the following examples:

a. An injector pen with a cartridge (e.g. 3 ml cylindrical glass cartridge) and a separate holder.
    b. An injector pen with a cartridge (e.g. 3 ml cylindrical glass cartridge) non-removably retained in a holder, so that the holder will be disposed of with the primary pack.
    c. An injector pen where the primary pack attaches directly to the pen, e.g. an injection-molded polymer cartridge.
    d. Any drug delivery device, with any type of reservoir or primary pack, e.g. inhaler, pouch.

The keying insert 1 with its coding features results in a number of advantages. For example, the proposed coded keying insert arrangements assist a user to distinguish between medicaments, thereby helping to ensure that a delivery device can only be used with a medicament for which the device is intended. Therefore, with the system applied to a cartridge assembly 20, the cartridge assembly 20 is prevented from being confused with any other drug by loading a cartridge assembly 20 with an incorrect or unwanted interface. The described coded keying insert 1 prevents a user from completing one or more of the following actions: fully inserting the cartridge assembly 20 into an incorrect cartridge holder 14 or attaching the cartridge assembly 20 and/or cartridge holder 14 onto an incorrect dose setting mechanism.

The coded keying insert 1 also results in a low cost coding mechanism since the proposed keying inserts 1 do not require a large number of parts and can be manufactured in a cost effective manner. Moreover, there are quite a large number of different keying insert coding configurations between the keying insert 1 and the cartridge holder 14 that may be used. Consequently, with the proposed coded keying insert schemes, a large number of medicaments can be distinguished from one another. In addition, with the keying insert 1, if a user attempts to load an incorrect cartridge assembly 20 into a cartridge holder 14 designed for a different cartridge assembly, the user will be alerted at an early stage of the assembly process.

In addition, the system can be used to prevent errors during manufacturing, when inserting cartridge assembly 20 into disposable cartridge holders 14 or disposable devices 10. Because the materials of construction of the main body 5 and the second body 4 are drug compatible and the coding features are on these bodies there is no risk of drug contact with incompatible materials. Since the keying insert 1 is fixed to the inside of the cartridge 19 the coding features cannot be removed without destroying the cartridge assembly 20, thus making the design relatively tamper proof. Positioning the keying insert 1 inside the cartridge 19 eliminates the need to increase the outer diameter of the cartridge assembly 20 and thus existing filling and assembly equipment can be used. First dose accuracy is also increased by eliminating the potential for air pockets after filling with medicament.

Exemplary embodiments have been described. However, as those of skill in the art will recognize certain changes or modifications to such arrangements may be made. As just one example, certain coding elements of one of the preferred arrangements discussed herein may be taken from one arrangement and combined with certain coding arrangements of other arrangements.

Those skilled in the art will understand, however, that further changes, modifications, revisions and/or additions may be made to the presently disclosed arrangements without departing from the true scope and spirit of the present invention, which is defined by the claims.

The invention claimed is:

1. A cartridge assembly comprising a cartridge and a keying insert, where the keying insert is positioned within a distal opening of the cartridge abutting an inner wall of the cartridge, the keying insert comprising:
- a main body defining a bore, the main body extending from a proximal end to a distal end and where the bore is configured for receiving a septum,
- a side wall extending from the proximal end to the distal end and where at least a portion of the side wall is configured to form a seal with the inner wall inside of the cartridge containing a fluid,
- a pass through to allow dispensing of the fluid from the cartridge,
- and a coding feature being configured to cooperate with a corresponding coding feature provided by a fluid delivery device, the coding feature being located on the main body,
- where the keying insert and cartridge are arranged such that a portion of its proximal end is within the cartridge and a portion of its distal end is outside of the cartridge and where the coding feature is located on the distal end of the keying insert.

2. The cartridge assembly of claim 1 further comprising a pierceable septum.

3. The keying insert of claim 1 wherein the coding feature is provided along an end face and/or side wall of the keying insert.

4. The cartridge assembly of claim 1 wherein the coding feature is provided on the distal end of the main body.

5. The cartridge assembly of claim 1 wherein the coding feature comprises a plurality of indentations or slots and/or a plurality of protrusions or ribs.

6. The cartridge assembly of claim 1 wherein the material of construction of the main body is selected from the group consisting of natural rubber, synthetic rubber, polyurethane, and mixtures thereof.

7. The cartridge assembly of claim 1 further comprises a releasable coupling for mounting a dispense interface.

8. The cartridge assembly of claim 1 wherein said coding feature prevents the cartridge from rotating within a cartridge holder of a fluid delivery device.

9. A cartridge assembly of claim 1 wherein the cartridge comprises:
- a tubular barrel, said tubular barrel comprising a bung located near a proximal end of said tubular barrel and a neck portion defining a distal port and having an interior wall,
- wherein the keying insert cooperates with the interior wall of the tubular barrel to form the seal, and wherein the coding feature located on a distal end protrudes from the neck portion.

10. A fluid delivery system comprising a cartridge assembly of claim 1 and a drug delivery device.

11. The cartridge assembly of claim 1 wherein the keying insert comprises one or more indicia to identify the fluid contained with the cartridge or to identify a corresponding fluid delivery device.

12. The cartridge assembly of claim 11 wherein the indicia is selected from the group comprising color, tactile, smell, text, symbols, and combinations thereof.

13. The cartridge assembly of claim 11 wherein the indicia is located on the main body and/or on a second body.

14. The cartridge assembly of claim 11 wherein the indicia is located on the distal end of the main body extending outside of the cartridge and/or on a portion of the second body that extends outside of the cartridge.

15. A cartridge assembly comprising a cartridge and a keying insert, where the keying insert is positioned within a distal opening of the cartridge abutting an inner wall of the cartridge, the keying insert comprising:
- a main body defining a bore, the main body extending from a proximal end to a distal end and where the bore is configured for receiving a septum,
- a side wall extending from the proximal end to the distal end and where at least a portion of the side wall is configured to form the seal with the inner wall of the cartridge containing a fluid,
- a pass through to allow dispensing of the fluid from the cartridge,
- a second body in sealing relationship to the main body,
- and a coding feature being configured to cooperate with a corresponding coding feature provided by a fluid delivery device, the coding feature being located on the second body,
- where the keying insert is configured such that a portion of its proximal end is within the cartridge and a portion of its distal end is outside of the cartridge and where the coding feature is located on the distal end of the keying insert.

16. The cartridge assembly of claim 15 wherein the coding feature is provided along an end face of the second body.

17. The cartridge assembly of claim 15 wherein the material of construction of the second body is selected from the group consisting of rubber, polyurethane, polyacetal (Delrin), ABS, polypropylene and mixtures thereof.

18. The cartridge assembly of claim 15 wherein the second body comprises a material of construction that is harder than the main body material of construction.

19. The cartridge assembly of claim 18 wherein the material of construction of the main body is rubber and the material of construction of the second body is polyacetal.

* * * * *